United States Patent
Kleihorst et al.

(10) Patent No.: US 10,327,643 B2
(45) Date of Patent: Jun. 25, 2019

(54) METHOD AND SYSTEM FOR VALIDATING AN ALARM SITUATION

(71) Applicant: Senso2Me NV, Kasterlee (BE)

(72) Inventors: Richard Kleihorst, Kasterlee (BE); Alain Van Buyten, Knokke-Heist (BE); Ben Schueler, Veldhoven (NL); Stefan Debois, Edegem (BE); Wilfried Philips, Lebbeke (BE)

(73) Assignee: SENSO2ME NV, Kasterlee (BE)

( * ) Notice: Subject to any disclaimer, the term of this patent is extended or adjusted under 35 U.S.C. 154(b) by 0 days.

(21) Appl. No.: 15/978,771

(22) Filed: May 14, 2018

(65) Prior Publication Data

US 2018/0330602 A1 Nov. 15, 2018

(30) Foreign Application Priority Data

May 12, 2017 (BE) .................................. 2017/5354

(51) Int. Cl.
*G08B 21/04* (2006.01)
*A61B 5/00* (2006.01)
(Continued)

(52) U.S. Cl.
CPC .......... *A61B 5/0022* (2013.01); *A61B 5/0002* (2013.01); *G08B 21/02* (2013.01);
(Continued)

(58) Field of Classification Search
CPC ... A61B 5/0002; A61B 5/0022; A61B 5/0024; G06F 19/00; G06F 19/30; G06F 19/32;
(Continued)

(56) References Cited

U.S. PATENT DOCUMENTS 6,313,743 B1    11/2001  Abraham-Fuchs et al.
7,714,728 B2 *   5/2010  Koblasz .............. G06F 19/3418
                                                      340/573.1
(Continued)

FOREIGN PATENT DOCUMENTS

DE    102014100642 A1    7/2014
EP         2983148 A1    2/2016
WO         9906979 A1    2/1999

OTHER PUBLICATIONS

Belgian Search Report from BE Application No. BE 201705354, dated Jan. 4, 2018.

*Primary Examiner* — Van T Trieu
(74) *Attorney, Agent, or Firm* — Workman Nydegger (57) ABSTRACT

A method for validating an alarm situation in a home includes determining by a processing unit of an alarm situation on the basis of data received from the home provided with a sensor network comprising one or more sensors and a central unit; transmission by the processing unit of a message to a care provider that an alarm situation is occurring at the occupant; sending out of a notification signal by the processing unit to the central unit; upon receiving the notification signal in the central unit, switching on an increased vigilance mode, wherein a call from the one or more care providers is prepared in the central unit by making available an audio function in one or more sensors of the sensor network; validating the alarm situation by establishing a conversation between one of the care providers and the occupant via the at least one sensor.

14 Claims, 6 Drawing Sheets

(51) Int. Cl.
*G08B 21/02* (2006.01)
*G08B 1/08* (2006.01)
*G08B 25/08* (2006.01)
*G08B 25/01* (2006.01)
*G08B 27/00* (2006.01)
*G08B 29/18* (2006.01)

(52) U.S. Cl.
CPC ......... *G08B 21/04* (2013.01); *G08B 21/0438* (2013.01); *G08B 21/0446* (2013.01); *G08B 1/08* (2013.01); *G08B 21/0208* (2013.01); *G08B 21/043* (2013.01); *G08B 21/0476* (2013.01); *G08B 25/01* (2013.01); *G08B 25/014* (2013.01); *G08B 25/08* (2013.01); *G08B 27/00* (2013.01); *G08B 29/18* (2013.01); *G08B 29/185* (2013.01)

(58) Field of Classification Search
CPC .... G06F 19/324; G06F 19/34; G06F 19/3418; G08B 21/04; G08B 21/0438; G08B 21/0446; G08B 21/0453; G08B 21/0461
See application file for complete search history.

(56) References Cited

U.S. PATENT DOCUMENTS

| | | | |
|---|---|---|---|
| 7,733,224 B2* | 6/2010 | Tran | G06F 19/3418 340/540 |
| 8,461,988 B2* | 6/2013 | Tran | G06F 19/3418 340/540 |
| 8,525,687 B2* | 9/2013 | Tran | G06F 19/3418 340/669 |
| 2002/0005894 A1 | 1/2002 | Foodman et al. | |
| 2007/0109114 A1 | 5/2007 | Farley et al. | |
| 2007/0191025 A1* | 8/2007 | McBrierty | G01S 5/0027 455/456.2 |
| 2008/0294462 A1* | 11/2008 | Nuhaan | G06Q 10/063114 705/3 |
| 2008/0294490 A1* | 11/2008 | Nuhaan | G06Q 10/063114 705/7.15 |
| 2014/0221797 A1* | 8/2014 | Bailey | A61B 5/0002 600/324 |
| 2015/0154850 A1 | 6/2015 | Fadell et al. | |

* cited by examiner

METHOD AND SYSTEM FOR VALIDATING AN ALARM SITUATION

FIELD OF THE INVENTION

The present invention is generally related to the field of wireless monitoring systems, in particular for the monitoring of one or more persons in a home. More specifically, the invention relates to responding after the signalling of an alarm situation.

BACKGROUND OF THE INVENTION

Personal alarm systems are systems that monitor vulnerable persons to detect certain situations or actions, such as possible falls, conspicuous behaviour or pressing an alarm button. They are widely used to allow vulnerable people (e.g. the elderly) to live safely in their homes or service flats for longer. Warnings are transmitted to a manned control room, which is expected to investigate the situation further and take any necessary action.

To be able to exclude false alarms and determine the specific help needed, a validation is carried out. This can be done by listening and voice interaction with the vulnerable person. In conventional systems classic telephone or VoIP lines are used for this purpose. These are used in case an actual alarm is detected or occurs at the location of the vulnerable persons. In other words, the personal alarm system establishes the call to the control room and the control room ends the call. In order to carry out a second call after a successful relief action, another procedure must be followed to call the control room from the location of the vulnerable person. In practice, this is done using a timer that automatically calls the control room again, e.g. 30 minutes after the event that triggered the alarm. This timer must be reset by manually pressing a specific button at the location of the person.

The purpose of the listening/voice interaction with the vulnerable person is to validate the alarm (and filter out false alarms) and to determine the specific needs and urgency of the call. It also reassures the person that effective assistance is on the way. The listening/voice interaction can be performed, for example, with a personal alarm device such as the Bosch CRS-H61-EU. This device is placed in a location in the person's house and is connected to the telephone line. Usually this is not near the place where the person has fallen or is in distress, with the result that the vulnerable person cannot effectively participate in the telephone call. Alternatively, a standard or mobile phone of the person can be used. This may be located at a place closer to the location of the fall but must be able to be picked up by the vulnerable person, because this call always leaves from the control room.

Wireless network systems, for example, wireless communication systems or wireless sensor systems, where a plurality of transmission units send data to one or more receiver units by means of wireless signals, are known in the prior art.

These network systems can occur in all kinds of configurations. Well-known examples include star networks, where each transmission unit communicates directly with a single receiver unit, often referred to in professional literature as a 'central unit', and mesh networks, where some of the transmission units also act as receivers and can forward signals.

A wireless network system is one of the possible implementations of the sensor network described in DE10 2014 100 642. This document describes a system consisting of a plurality of sensors for detecting acoustic and/or optical signals. The sensors have both loudspeaker and microphone functionality. A central unit, implemented as a central bus connected to a sensor bus, receives and processes the signals from the sensors. The central bus can be directly connected to sensors. Each 'bus participant' is connected to the sensor bus and thus to the sensors. The central bus and the bus participant comprise an actuator which is used for performing acoustic, optical or electrical signals.

By providing sensors through which audio communication can be effected, the above-mentioned problem—that the vulnerable person cannot access a telephone in case of emergency, for example due to a fall, to report the emergency situation—is resolved. The listening/speech function in the sensor thus increases the physical safety of the vulnerable person.

However, the solution disclosed in DE10 2014 100 642 has some important drawbacks. The proposed system consumes a lot of power because the sensors with microphone function are constantly on and because a lot of computationally-intensive tasks have to be carried out during processing to process the incoming sensor signals. It is stated that in some embodiments this processing can even partly be done in the sensors, because the amount of data that has to be transported over the bus is thus reduced.

Due to the statistical processing of the sensor signals, the received sensor signals (including the acoustic signals) must be transmitted time-synchronously to the central unit in the proposed system. It is emphasised that strict time-synchronicity of the microphone signals is crucial for the proper functioning of the system. It is clear that this can only be done at the expense of greater power consumption.

US2002/005894 discloses a system for detecting an event within a premises and for providing data such as live or recorded video, audio and data regarding that event to a website. The event may be an unauthorized entry to the premises, a fire or a maintenance malfunction within the premises. The website may be accessed by a variety of authorized users including the owner or manager of the premises, a central monitor, local police, fire or emergency medical personnel, or other entities specified by the owner or manager of the premises. The system permits authorized users to view the event in real time or as recorded on the website after the event has occurred to determine the type of event and an appropriate course of action to rectify it. In case an alarm situation is detected at the premises, a system controller in the premises is activated, which then opens a two-way combined data, audio and video channel to the website. Also a signal is transmitted locally to turn on a particular camera that covers the tripped detector. The document however remains silent on how a conversation between an individual at the premises and the central monitor is set up.

Consequently, there is a need for a power-efficient system in which one or more of the aforementioned disadvantages are avoided or solved and in which the privacy of the monitored person is always respected.

SUMMARY OF THE INVENTION

It is an object of embodiments of the present invention to provide for a personal alarm system capable of performing a verification of a generated alarm in an energy efficient manner. It is also an aim of embodiments of the present invention to propose a method for performing such verification.

The above objective is accomplished by a method and system according to the present invention as described below.

In a first aspect the invention relates to a method for remote validation of an alarm situation of a person in a home. The method comprises the following steps:
- determining by a server/processing unit of an alarm situation on the basis of data received from the home provided with a sensor network comprising one or more sensors and a central unit,
- transmission by the server/processing unit of a notification to one or more care providers that an alarm situation is occurring at the person,
- sending out of a notification signal by the server/processing unit to the central unit,
- upon receiving said notification signal in the central unit, switching on an increased vigilance mode, wherein a call from the one or more care providers is prepared in the central unit by making available an audio function in one or more sensors of the sensor network,
- validating the alarm situation by establishing a conversation between said one of the care providers and the person via said one or more sensors.

The proposed solution indeed allows for a validation of the generated alarm in an ethical and very energy-efficient way. Because the central unit only switches on the audio part of the monitoring system when a notification signal is received, power consumption is limited. Moreover, in the proposed approach it is possible to specifically activate only one or a few sensors of the sensor network for audio functionality.

In a preferred embodiment the method further comprises a step in which the one or more care providers are informed that the increased vigilance mode is switched on.

In a preferred embodiment the method further comprises a step in which, after the conversation between the one of the care providers and the vulnerable person has been finished, the increased vigilance mode is activated again.

In one embodiment an audio amplifier in the central unit is switched on when the alarm mode is switched on.

In another embodiment the location is determined where the alarm situation was reported from based on the received data. In an advantageous embodiment the audio function of the nearest sensor is activated via this position determination.

In an embodiment switching on the increased vigilance mode comprises increasing the frequency at which the connection between the sensors and the central unit is checked.

In a further embodiment, during the conversation between one of the care providers and the vulnerable person, a light is illuminated in the one or more sensors along which the conversation proceeds.

In another aspect the invention relates to a wireless monitoring system for monitoring a person in a home. The system includes a central unit and one or more sensors connected in a wireless sensor network, wherein the central unit is adapted to receive wireless data which is transmitted by each of the sensors and to execute signals and wherein the central unit is further adapted in order to activate an increased vigilance mode when receiving a notification signal in the sensor network, which enables an incoming telephone call to be received and an audio function of one or more of the sensors to be prepared and effectively operationalised.

In a preferred embodiment the sensors in a star network are connected to the central unit. In an advantageous alternative embodiment the topology of a mesh network is proposed.

In a typical embodiment the sensors are arranged to generate ringtones when a call comes in.

In a further embodiment at least one sensor is adapted to provide audio functionality and at least one functionality of motion detection, light detection and temperature detection.

In another embodiment the central unit has microphone and loudspeaker functionality.

In a further aspect the invention also relates to a system comprising a wireless monitoring system as described above and a processing unit, i.e. a server, adapted for determining an alarm situation on the basis of data received from the home provided with the wireless monitoring system, for transmitting to one or more care providers of a notification that an alarm situation is occurring and for sending out a notification signal to the central unit to switch to the increased vigilance mode in the sensor network.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The above and other aspects of the invention will be apparent from and elucidated with reference to the embodiment(s) described hereinafter.

BRIEF DESCRIPTION OF THE DRAWINGS

The invention will now be described further, by way of example, with reference to the accompanying drawings, wherein like reference numerals refer to like elements in the various figures.

DETAILED DESCRIPTION OF ILLUSTRATIVE EMBODIMENTS

The present invention will be described with respect to particular embodiments and with reference to certain drawings but the invention is not limited thereto but only by the claims.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

It should be noted that the use of particular terminology when describing certain features or aspects of the invention should not be taken to imply that the terminology is being re-defined herein to be restricted to include any specific characteristics of the features or aspects of the invention with which that terminology is associated.

In the description provided herein, numerous specific details are set forth. However, it is understood that embodiments of the invention may be practiced without these specific details. In other instances, well-known methods, structures and techniques have not been shown in detail in order not to obscure an understanding of this description.

The present invention relates to a method and system for remotely validating an emergency situation in a home after it has been detected in a server that can monitor events in the home.

Figure 1:
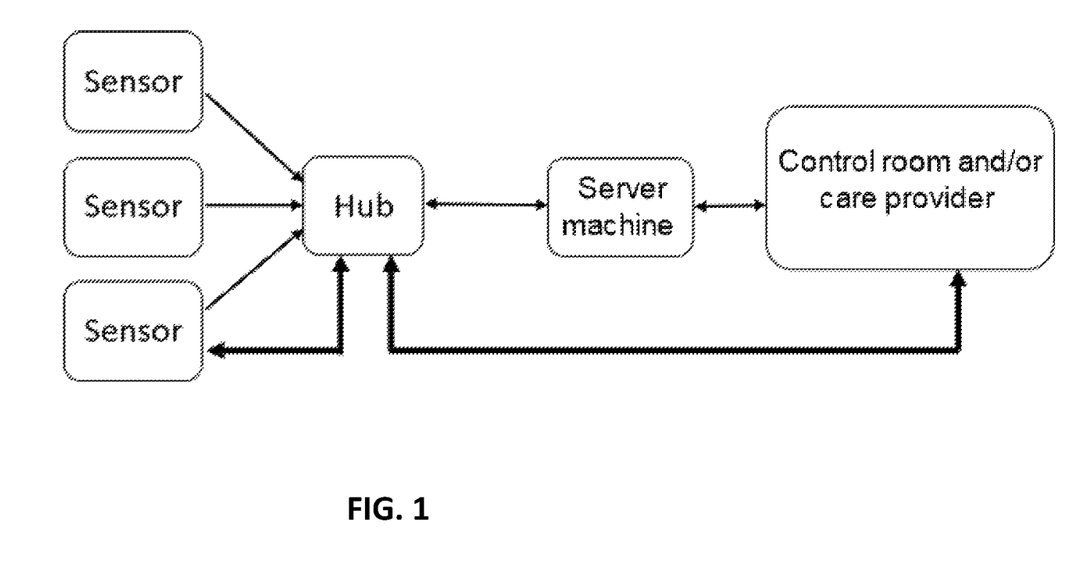
FIG. 1 illustrates a monitoring system as considered in the present invention.

A monitoring system is considered as shown in FIG. 1, comprising a central unit ('hub' in FIG. 1 and often referred to as such in the rest of this description) and a wireless network of sensors. The central unit and the set of sensors are placed in the home of the person in question, for example an elderly person. The sensors are preferably set up in the rooms where the occupant lives the most and/or where there is a potential danger of falling, for example. Each sensor has a unique location in the home. The central unit can receive data originating from the sensors wirelessly. The central unit also forms the connection between the sensor network and the control room. Both the control room and the central unit are connected to a server that is responsible for processing the incoming data and, if necessary, for further action.

The central unit operates as a hub in the sensor network, which in a preferred embodiment is implemented as a wireless star network. Other embodiments of the network are, however, also possible. Particularly interesting alternatives to a star network are mesh networks or bidirectional networks. The communication between transmission and receiver units can take place according to a communication standard such as Zigbee, Bluetooth, DECT-ULE, Z-wave or Wi-Fi. The central unit collects the information provided by the sensors. This information can relate to movement, light, temperature and the status of a push button that is connected to a sensor. The sensors include a microcontroller to read out the received measurements and to transmit them to the central unit. The central unit includes, among other things, a microcontroller and a timer. This allows, among other things, to provide information received from sensors with a timestamp.

Motion sensors allow it to be determined which room of the home the vulnerable person is in or is moving in, at least as far as the rooms are concerned that are equipped with such a sensor. The movement can be reported quickly and reliably to the central unit of the monitoring system and thus further to the server. The information from motion sensors also allows determining quite accurately the time that the person needs to move from one room to another. A light sensor can be, for example, a visible light detector or a daylight sensor. Such a sensor can, for example, detect whether a light is switched on in the course of the night in a specific room. Temperature sensors allow the temperature in a specific room to be monitored. After all, the temperature can have an effect on the behaviour of the person. In an extreme case, the temperature sensor can also detect a fire. Sensors can also be provided with a push button, which, when pressed, ensures that a direct alarm message is sent to the central unit via the microcontroller in the sensor.

The microcontroller contained in the sensors is typically programmable and adapted to execute a program from a memory. The microcontroller can be placed in a sleep mode to save energy. To wake up the microcontroller from sleep mode, the sensor contains a watchdog timer. The watchdog timer awakens the microcontroller when it receives a specific signal, e.g. an interrupt. Furthermore, the sensors have an RF circuit suitable for one-way communication to transmit data wirelessly to the central unit. A local battery provides power. Due to the small size of the sensor, the battery has a rather limited capacity. Each sensor has a unique identification value stored in a non-volatile memory.

The sensor signals reach the server via the central unit, which functions among other things as a processing unit. The server is equipped with software for analysing the information that comes in from the sensors. The server can perform the necessary calculations based on this input to analyse the location of the person. The server can also evaluate movement events via the analysis software based on the input, for example by calculating one or more mobility values based on a time difference between a last movement detected by a first wireless sensor and a first movement detected by another wireless sensor. The analysis software (sometimes also referred to as 'data analysis program') is based on the assumption that each wireless signalling device is associated with a particular type of room or space. The software is also able to calculate, on the basis of information from motion sensors, the time a person needs to move from room A (e.g. the living room) to room B (e.g. the bedroom). By measuring this time over a longer period (e.g. a week or several weeks, months or years), mobility patterns can be derived. It is also possible to deduce from the data from the sensors the use of the rooms by the so-called 'activities of daily living' pattern during the day. This can for example indicate how long people sleep, how many times and how long they go to the bathroom, how many times they are in the kitchen, whether there is activity there, and whether they go outside. All this mobility information can be stored in a database and used for further analysis.

Based on the incoming information from the sensors and the information from the database, the server can detect a possible alarm situation. This can be derived, for example, from mobility values that suddenly deviate strongly from the usual mobility patterns as registered in the database. Another possible scenario is that a signal is received from a push button on a sensor. Such 'life data' can directly indicate an emergency situation. Some concrete examples could be: if the occupant is occupied in a bathroom (possibly even active) in a bathroom, i.e. deviating too much from the registered 'reference value', they may have fallen there. If there is no activity in the living room or kitchen for too long, this may also give cause for alarm. Not out of bed on time can also be reason for an alarm, as might be too long away from home. It is a combination of the sensor data, from the sequence of triggering to the non-triggering of certain sensors, which can lead to the decision as to whether or not a possible alarm situation occurs.

Upon detection of a possible alarm situation, the server generates an alarm signal. The present invention relates to what happens next with such a generated alarm signal to validate the emergency situation, i.e. to check whether there is an actual problem or whether it is a false alarm.

In the invention, the wireless sensor network is also equipped with microphone and loudspeaker functionality. In an embodiment separate sensors with microphone and loudspeaker function are used in the network, in addition to the already mentioned sensors for detection of light, movement and/or temperature. In this case, the audio sensors and other sensors should of course not be placed too far apart in order to allow the location determination to retain its full meaning. In another embodiment the microphone and loudspeaker functionality are integrated, and the sensors thus also become audio devices. This means that the sensors contain not only the necessary electronics to perform the sensing, but also electronics for setting up a wireless audio conversion: microphone function, loudspeaker and two-way radio communication. The provision of such a wireless sensor network with sensors with audio functionality is an essential contribution to the prevention of the aforementioned problem of a telephone set being out of range when an emergency situation occurs. In order to achieve the aforementioned goal of the lowest possible energy consumption and to save as much battery energy as possible, only the part of the sensor network meant for sensing movement, light and/or temperature is always active. In an extreme form the sensor network is formed by only one audio sensor and one sensor that detects movement, light and/or temperature. This audio sensor and other sensor can then still be integrated. The audio portion of the sensor network is only turned on in specific circumstances as explained in detail below.

The monitoring system of FIG. 1 measures the environment with the help of one or more sensors that collect the information in the hub. This passes this information on to a server. The server is connected to care providers and/or a control room. From the control room an audio validation can be performed by establishing audio contact with the hub. The hub will pass this connection to one or more audio sensors.

Alternatively, the audio contact can be established from a different location than the control room, e.g. by a care provider or a confidential adviser of the occupant, who has permission to establish such an audio contact and as such is also known in the monitoring system.

As explained above, the server is able to determine the most likely location of the occupant in the home based on the available information. This information is then used to establish a voice connection to the nearest sensor. Alternatively, several sensors in the vicinity of the determined location in the home can also be prepared for voice communication. This has the advantage that the chance of speaking with the occupant can only increase. By speaking with the occupant, it becomes possible to drastically reduce the number of false alarms.

In the method proposed in this invention, following the generation of an alarm, the following actions are performed by the server.

The server informs one or more persons, e.g. relatives or friends of the occupant or, possibly via a control room, one or more care providers in a notification that a possible alarm situation is occurring at the person in the home and that it needs to be verified. The server has stored the necessary data for this purpose in a memory.

Furthermore, the server gives permission to the wireless monitoring system in the home to receive a call. To this end, the server sends a notification message to the monitoring system in the home, in particular to its central unit. This is an important element in the proposed method: as long as no 'permission' has been given by the server, the audio part of the monitoring system, and more specifically of the sensor network, will remain switched off and there will be no energy consumption. Furthermore, this characteristic is advantageous in connection with respecting the privacy of the occupant. If there are multiple wake-up levels in the system, the server can use the central unit to bring the sensors to a higher level of activity (i.e. a level of increased vigilance) (whereby more energy is consumed), by which the sensors are informed that there may be a call coming. This is explained in more detail later in this description.

The audio part of the sensor operates according to a wake-up principle where it listens at set times (for example every 30 seconds, or every minute or every 2 or 5 minutes) if the central unit is trying to transmit an incoming call. In particular embodiments it is also possible to work with multiple levels to get out of a sleep mode. This is advantageous as it shortens the response time and further optimises the power consumption. An example application can be the following. When the server decides to generate an alarm based on the available data, it informs the central unit by means of a notification message that the audio part of the sensors must leave a state in which the audio sensor checks, for example, only every few minutes if the hub is trying to make contact with the audio sensor (this is the so-called deep sleep mode). The audio sensor then enters an increased vigilance mode ('alerted mode') in which, for example, every 10 seconds a check is made whether a call is being transmitted from the central unit. The audio function of one (or more) sensors is now made available for effective use during a call. When an incoming call is detected, the audio sensor automatically answers it and thereby enters an operational mode (i.e., 'call mode'). After the call is finished, the audio sensor can remain in the increased vigilance mode, as more calls may follow. When the alarm situation has been fully completed, the server informs the central unit that the sensors may go back into deep sleep mode.

Figure 2:
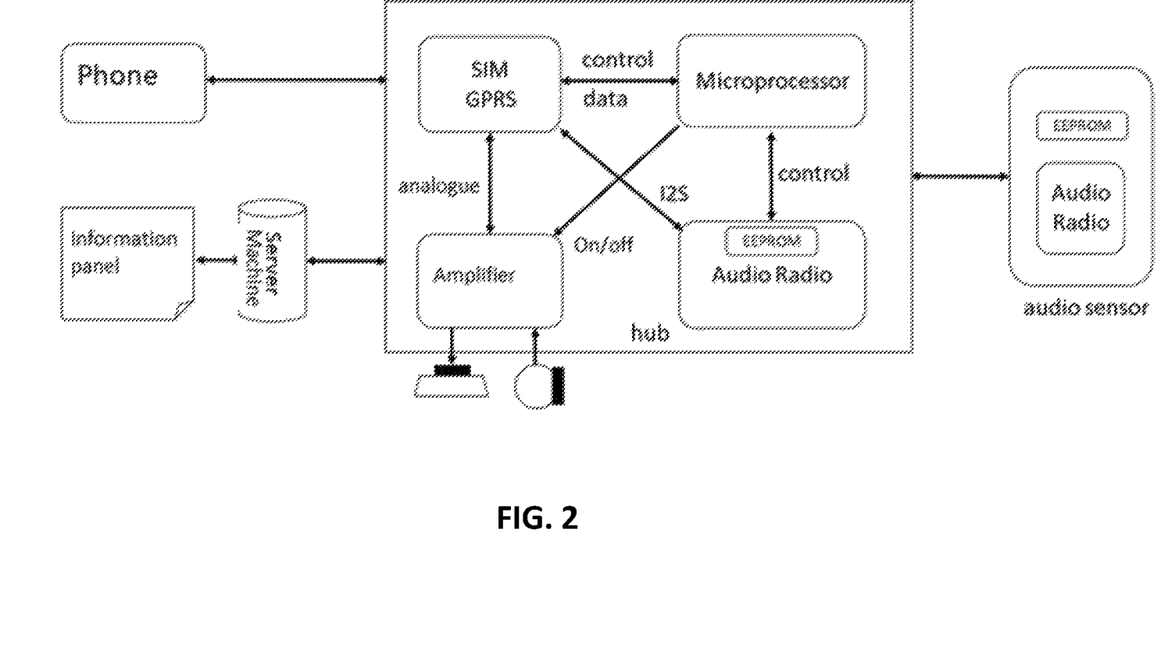
FIG. 2 illustrates the main parts of the monitoring system.

FIG. 2 gives an overview of an implementation of the considered system.

The call from one of the confidential advisers or care providers who were notified of the emergency situation comes in via the hub, i.e. the central unit. In an embodiment, this call can take place over a data connection via the well-known VoIP protocol. Note that in this case the transmission of sensor data can continue during the call. If VoIP runs via UTP, an extra data channel is available. In another embodiment, the call may arrive via the mobile connection of the hub (e.g., 2G or 4G) via a SIM card with telephone number in the 'GPRS/SIM' module in FIG. 2. In all circumstances it must be ensured that a communication path remains available for the voice data as well as for the sensor data. In some embodiments, one path can be shared for both speech and data.

The server receives the sensor data from the central unit. The main tasks of the server are:
- taking decisions about possible alarm situations
- maintaining administrative data
- the generation of analysis results concerning the status of the sensors and their environment to be displayed to users on an information panel (see FIG. 2) connected to the server
- inform the interested parties (care provider(s) and/or relatives(s)) of a possible alarm situation In an embodiment the server is implemented as a cloud-based service. In another embodiment the server is a physical device that is placed, for example, in a residential care centre or block of flats where many elderly people live.

The connection between the hub and the server is bidirectional. In the embodiment shown in FIG. 2, the central unit has four functional blocks. A module with a SIM card can be used for data and voice communication. Furthermore, the central unit contains an interface module for voice communication (indicated by 'Audio Radio' in FIG. 2). This interface module includes a memory (e.g. an EEPROM as in FIG. 2) to store an identification of the connected audio sensors. Only these audio sensors can then be contacted by the hub. Audio sensors of other hubs thus remain shielded. Furthermore, the interface module contains a microcontroller. A microprocessor, for example an ARM processor, monitors the operation of the hub. This microprocessor is able to communicate with the SIM/GPRS module and the interface module, among other things, to exchange control messages. The microprocessor also ensures that the data received from the sensors is transmitted. The amplifier block in FIG. 2 is optional and serves to amplify the audio signal to a loudspeaker which may be provided in the central unit. The central unit can thus also be provided with the necessary functionality for audio communication. This can be useful, for example, in case none of the audio sensors are available. The SIM/GPRS module then ensures the establishment of the analogue audio connection with the loudspeaker and microphone in the hub. The processor can control the amplifier. In an embodiment the amplifier can be implemented as a class-D amplifier. This again means a contribution to energy efficiency.

In an embodiment as shown in FIG. 2, the SIM/GPRS module can connect to the interface module via a digital route, represented by the 'I2S' (Inter-IC Sound) protocol for communication of audio data (by way of example), which is capable of transmitting duplex or half-duplex audio signals to an audio sensor.

From the interface module there is a two-way connection with the corresponding interface module (see FIG. 2, again referred to as 'Audio Radio') in the audio sensor. This interface module in the audio sensor is also equipped with a microcontroller and a memory, e.g. an EEPROM. The audio sensor can make duplex or half-duplex audio connections via the interface module. Again, the data in the EEPROM memory ensures that the audio sensor can only connect to the corresponding hub and not to other hubs. The microcontroller runs dedicated software. With this software, the battery status of the sensor is also monitored, among other things. All interface modules of the sensors are linked to the interface module of the central unit with which the sensors are connected.

In a preferred embodiment all connections (indicated by arrows in FIG. 2) are wireless.

A successful call to perform a validation can only occur when an alarm has been generated by the server, in particular, from the moment that the alarm is detected in the server until the server is informed that the relevant alarm has been fully processed.

In an advantageous embodiment a call is initiated by means of a few ringtones on the audio sensor(s) to which the call is transmitted. The end of the call can be indicated via an 'end connection' tone. In an embodiment it can be indicated whether a call is in progress with an LED light in the housing of the audio sensor.

Figure 3:
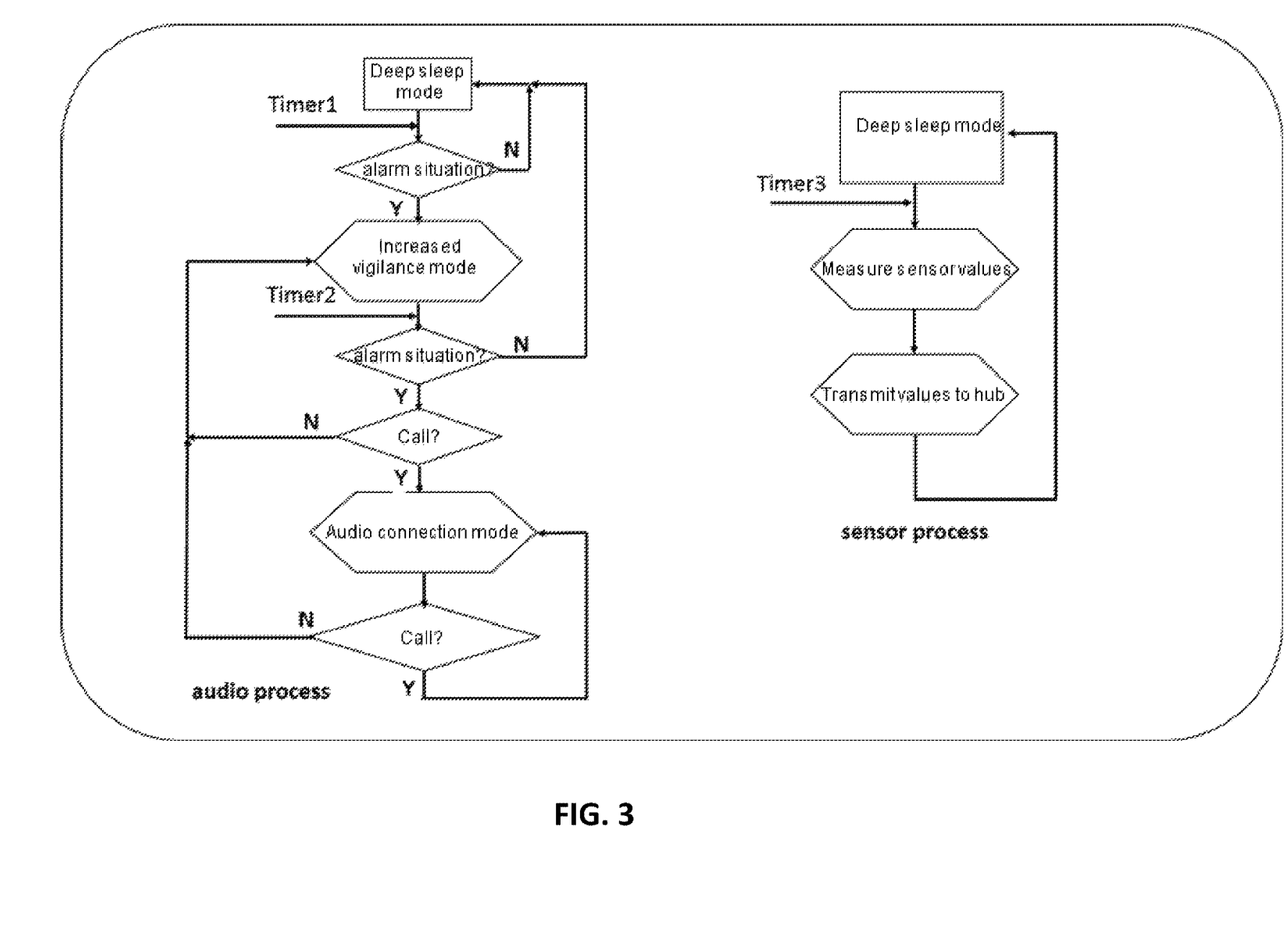
FIG. 3 illustrates an operating process according to an embodiment of the proposed method.

In FIG. 3 a possible scenario of a work process according to the present invention is illustrated. Normally, the audio sensors are in deep sleep mode and are periodically awakened by Timer1 with a long interval. At that moment, they briefly wait for a message from the hub, via the interface module 'Audio Radio', whether they should switch to an increased vigilance mode. If not, they will go back to deep sleep mode. In the increased vigilance mode, the audio sensor will be periodically awakened by Timer2 with a shorter interval. At that moment the audio sensors will wait a moment for a message from the hub to make an audio connection. If so, they will answer the audio connection themselves. After the call has ended, the audio sensor will preferably return to the increased vigilance mode. After all, there may be more conversations to follow. If the hub indicates that this mode may be turned off, the audio sensor will return to deep sleep mode. With an audio sensor that also measures environmental parameters, a second process is active, namely a measuring process that periodically (according to Timer3, i.e. the previously-mentioned watchdog timer) measures environmental parameters and transmits them to the hub. This is illustrated on the right side of FIG. 3.

Figure 4:
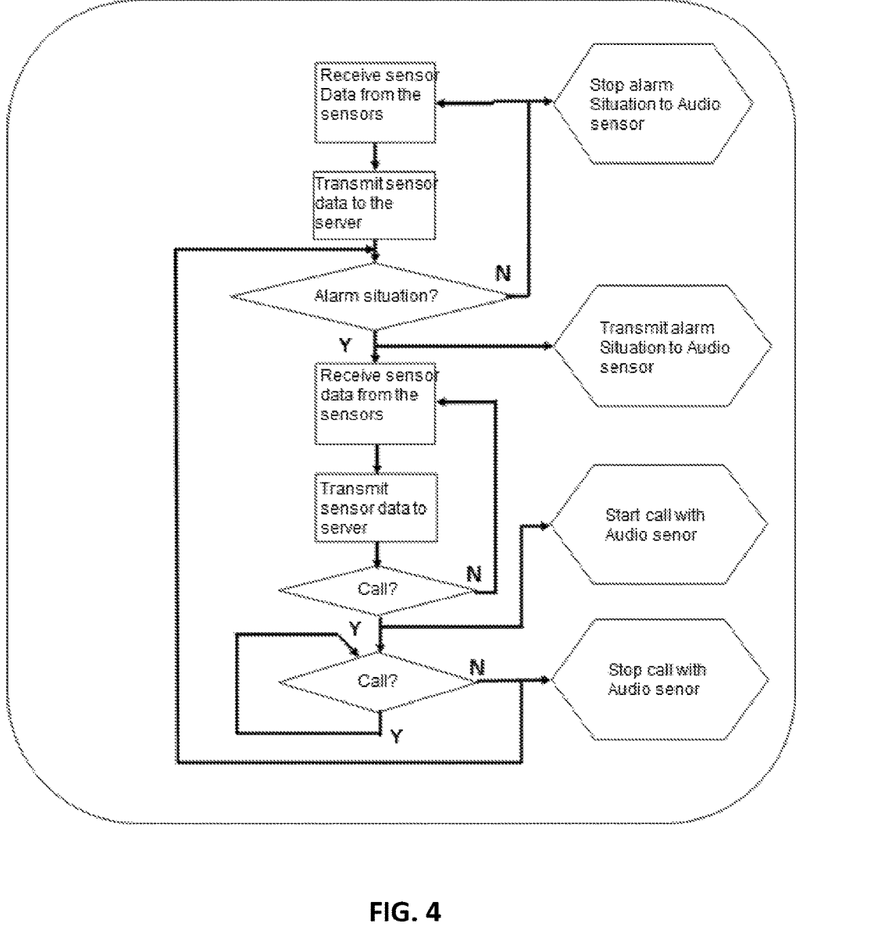
FIG. 4 illustrates an operating process for a scenario where the hub comprises a 2G communication module.

FIG. 4 describes an embodiment for the case in which a 2G connection is available. As already mentioned, the hub has the function, among others, of transmitting sensor data to the server and sporadically maintaining an audio connection with a telephone. In its normal operation, there is two-way communication between the hub and the server where sensor data packets are transmitted, and control data is received. If the hub of the server is notified of a possible alarm situation, the hub instructs the audio sensors to enter an increased vigilance mode. The hub then continues to transmit sensor data to the server until the latter indicates that an audio connection is being made. Since a 2G module can only hold one data stream at a time, the hub will therefore disconnect the data connection with the server and wait until the 2G module is called. If a call is made, the hub answers and possibly transfers the audio communication to its own amplifier, loudspeaker and microphone. One or more audio sensors are now also called, which also answer themselves. If there has not been a call, the hub can also, after a time-out, return to a state in which sensor data is transmitted again. After there has been a call, the hub breaks the connection with the audio sensor(s) and returns to the state in which sensor data is transmitted to the server. As soon as the server indicates that the alarm situation is over, the hub informs the audio sensors that they may return to the deep sleep mode. The hub then goes back to the normal mode of transmitting sensor packets to the server.

Figure 5:
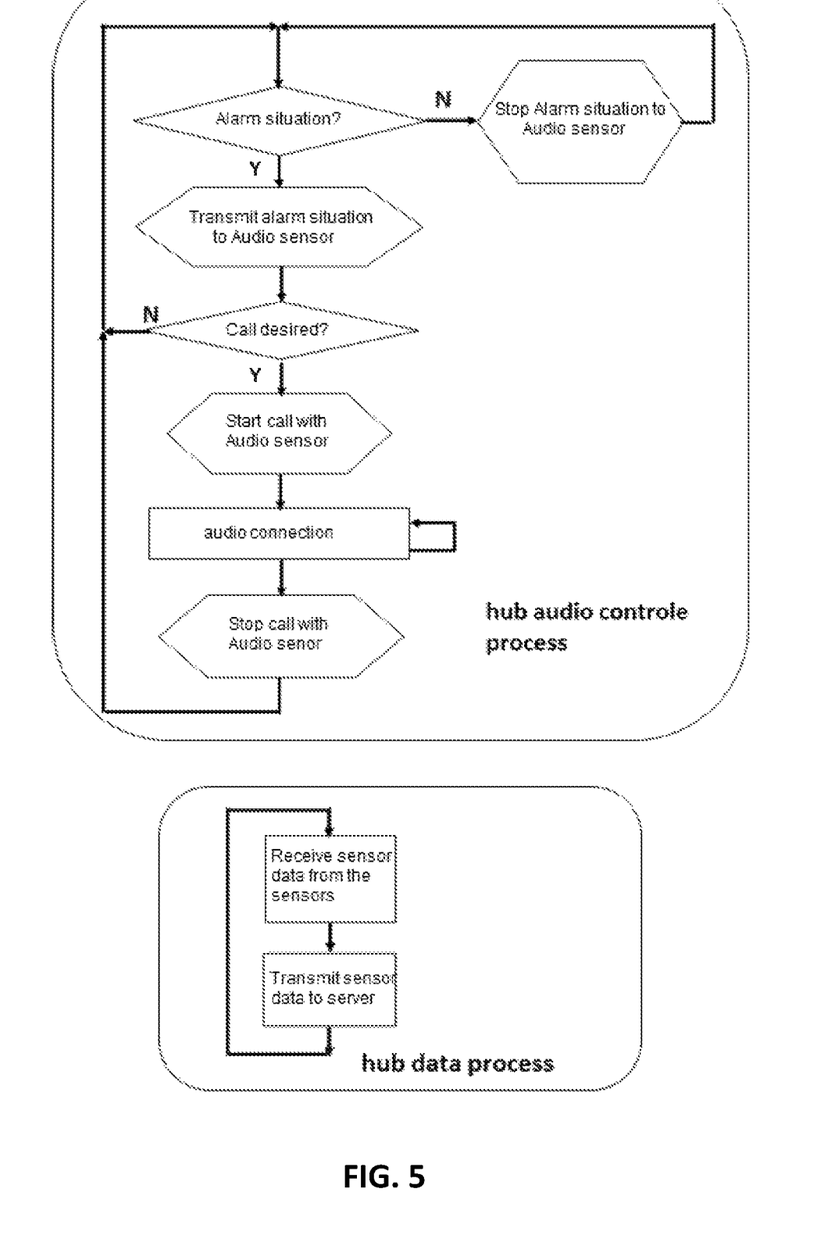
FIG. 5 illustrates an operating process for a scenario where the hub comprises a 4G communication module.

As already indicated, a communication path must be provided for the voice data and for the sensor data; possibly one path can be shared for both data transfers. FIG. 5 shows a flow chart that is applicable to the following cases:
- a 2G connection for audio and UTP (unshielded twisted pair, i.e. classical telephone line) for data
- a 4G connection for audio and data
- a 4G connection for audio with UTP for data
- audio via VOIP over UTP By way of example, the further operation illustrated in FIG. 5 will now be explained on the basis of a hub with 4G module or extra connection via UTP or Audio via VOIP over UTP. As already mentioned, the function of the hub remains transmitting sensor data to the server and sporadically maintaining an audio connection with a telephone. In the normal state, the hub carries out two-way communication with the server, where sensor data packets are transmitted, and control data is received. In this embodiment, this takes place in a separate process in which the connection with the server is maintained via a private link. This connection is not broken when establishing an audio connection with a telephone. If the hub of the server is notified of a possible alarm situation, the hub instructs the audio sensors to enter the increased vigilance mode. The hub is ready until a call is made to the 4G module or via VoIP over the UTP connection. If a call is made, the hub answers and possibly transfers the audio to its own amplifier, loudspeaker and microphone. One or more audio sensors are also called, which also answer themselves. At the end of the call, the hub disconnects from the audio sensors. As soon as the server indicates that the alarm situation has been dealt with, the hub informs the audio sensors that they may return to the deep sleep mode.

Figure 6:
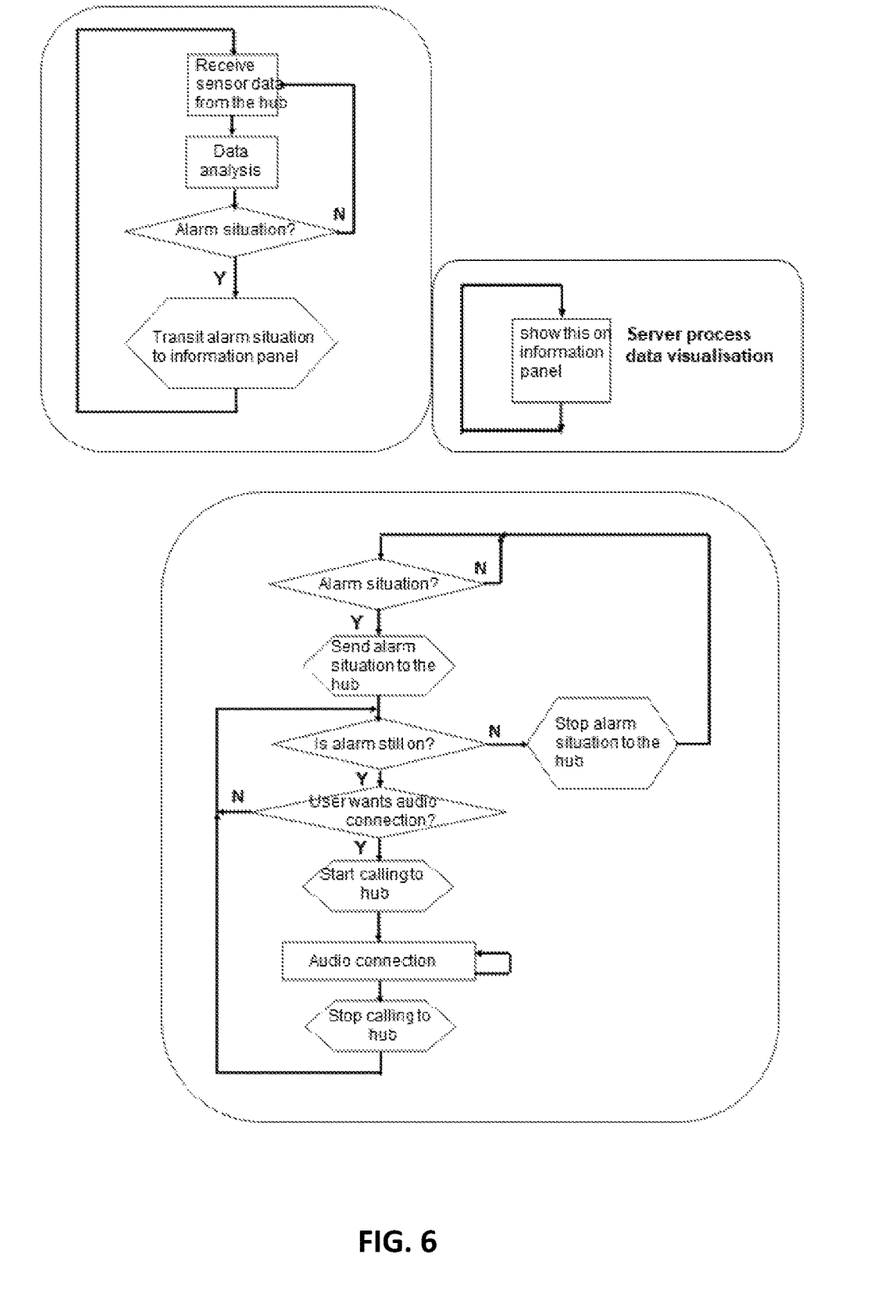
FIG. 6 illustrates processes that run on the server.

FIG. 6 illustrates the processes that run on the server. At the top left of the figure, the process is shown in which sensor data is received from the hub and processed in order to decide whether or not there is a possible alarm situation. In addition, the process is displayed to show the user information from the sensor data on an information panel. At the bottom, the handling of the validation of an alarm situation is summarised. In the event of an alarm situation, the server will inform the hub of this. On the information panel, the server now allows a user to call the hub via a classic telephone line or via VoIP. This possibility is offered by means of, for example, a button that has to be pushed or by displaying a telephone number. If the user believes that the alarm has been handled, the user will set the alarm to 'off' and the server will report to the hub that the alarm situation is over, i.e. has been handled.

While the invention has been illustrated and described in detail in the drawings and foregoing description, such illustration and description are to be considered illustrative or exemplary and not restrictive. The foregoing description details certain embodiments of the invention. It will be appreciated, however, that no matter how detailed the foregoing appears in text, the invention may be practiced in many ways. The invention is not limited to the disclosed embodiments.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for remote validation of an alarm situation at a person in a home, comprising:
    determining by a processing unit of an alarm situation on the basis of data received from said home provided with a sensor network comprising one or more sensors and a central unit,
    transmission by said processing unit of a notification to one or more care providers that an alarm situation is occurring at said person,
    sending out of a notification signal by said processing unit to said central unit,
    upon receiving said notification signal in said central unit, switching on an increased vigilance mode, wherein a call from said one or more care providers is prepared in said central unit by making available an audio function in one or more sensors of said sensor network,
    validating said alarm situation by establishing a conversation between one of said care providers and said person via said one or more sensors.

2. The method for remote validation as in claim 1, further comprising a step of communicating to said one or more care providers that said increased vigilance mode is switched on.

3. The method for remote validation as in claim 1, wherein after said conversation between said one of said care providers and said person is finished, said increased vigilance mode is returned to.

4. The method for remote validation as in claim 1, wherein an audio amplifier is switched on in said central unit when said call is established.

5. The method for remote validation as in claim 1, wherein on the basis of said received data a location determination is made of from where said alarm situation is reported.

6. The method for remote validation as in claim 5, wherein the audio function of the nearest sensor is activated by said location determination.

7. The method for remote validation as in claim 1, wherein switching on said increased vigilance mode comprises increasing the frequency with which the connection between said sensors and said central unit is controlled.

8. The method for remote validation as in claim 1, wherein during said conversation between said one of said care providers and said person, a light is lit in said one or more sensors along which the conversation proceeds.

9. A wireless monitoring system for monitoring a person in a home comprising a central unit and one or more sensors connected in a wireless sensor network, said central unit being adapted to receive wireless data transmitted by each of the sensors and execute signals, and
wherein said central unit is further adapted to activate an increased vigilance mode upon receipt of a notification signal in said sensor network, which enables an incoming telephone call to be received and an audio function of one or more of said sensors to be made available.

10. The wireless monitoring system as in claim 9, wherein said sensors in a star network are connected to said central unit.

11. The wireless monitoring system as in claim 9, wherein said sensors are adapted to generate ringtones when a call comes in.

12. The wireless monitoring system as in claim 9, wherein at least one sensor is adapted to provide audio functionality and at least one functionality of motion detection, light detection and temperature detection.

13. The wireless monitoring system as in claim 9, wherein said central unit has microphone and loudspeaker functionality.

14. A system comprising a wireless monitoring system as in claim 9 and a processing unit adapted for determining an alarm situation on the basis of data received from said home provided with said wireless monitoring system, for transmitting to one or more care providers of a warning that an alarm situation is occurring and for sending out a notification signal to said central unit to go to said increased vigilance mode in said sensor network.

* * * * *